(12) United States Patent
Comunale

(10) Patent No.: US 9,115,512 B2
(45) Date of Patent: Aug. 25, 2015

(54) "MATCH" CONTROLLED CONTAINER

(76) Inventor: Mark E. Comunale, Georgetown, MA (US)

( * ) Notice: Subject to any disclaimer, the term of this patent is extended or adjusted under 35 U.S.C. 154(b) by 394 days.

(21) Appl. No.: 11/150,223

(22) Filed: Jun. 13, 2005

(65) Prior Publication Data
US 2005/0285715 A1    Dec. 29, 2005

Related U.S. Application Data

(60) Provisional application No. 60/581,108, filed on Jun. 18, 2004.

(51) Int. Cl.
| | |
|---|---|
| *B60R 25/00* | (2013.01) |
| *E05B 73/00* | (2006.01) |
| *G07F 17/00* | (2006.01) |
| *G07F 17/12* | (2006.01) |
| *E05B 47/00* | (2006.01) |
| *E05B 65/52* | (2006.01) |
| *G06F 19/00* | (2011.01) |

(52) U.S. Cl.
CPC ............ *E05B 73/00* (2013.01); *G07F 17/0092* (2013.01); *G07F 17/12* (2013.01); *E05B 47/00* (2013.01); *E05B 65/52* (2013.01); *G06F 19/3462* (2013.01); *G06F 19/366* (2013.01)

(58) Field of Classification Search
CPC ........... G07C 9/00896; G07C 9/00571; G07C 9/00912; G07C 9/00103; G07C 9/00309; E05B 73/00; E05B 47/00; E05B 65/52; G07F 17/12; G07F 17/0092; G07F 19/366; G07F 19/3462
USPC .......... 340/5.73, 5.1, 5.2, 5.7, 5.71, 5.72, 5.8, 340/5.81, 5.82, 5.85

See application file for complete search history.

(56) References Cited

U.S. PATENT DOCUMENTS

| | | | | |
|---|---|---|---|---|
| 3,978,321 | A * | 8/1976 | Doggett | 340/933 |
| 4,457,240 | A * | 7/1984 | Hungerford | 109/45 |
| 5,736,782 | A * | 4/1998 | Schairer | 257/679 |
| 5,781,442 | A * | 7/1998 | Engleson et al. | 700/214 |
| 6,032,155 | A * | 2/2000 | de la Huerga | 1/1 |
| 2004/0039920 | A1* | 2/2004 | Kim et al. | 713/185 |
| 2004/0108938 | A1* | 6/2004 | Entrekin | 340/5.73 |
| 2005/0029341 | A1* | 2/2005 | Magee et al. | 235/379 |

* cited by examiner

*Primary Examiner* — Jennifer Mehmood
*Assistant Examiner* — Yong Hang Jiang
(74) *Attorney, Agent, or Firm* — Morris I. Pollack

(57) ABSTRACT

A secure safety container is made up with a base and a cover that can be locked together by an electric operated lock carried by the container. The top and base of the container together form a secure space within the container sized and configured to receive an article or articles. Also carried by the container are a CPU with a touch data entry screen, a rechargeable battery, date entry and infra red data entry ports, a tracking transponder and a thermister to provide humidity and temperature inputs to the CPU. After entry into the CPU of insert data relative to the article or articles to be secured within the secure space the electric lock may be activated to secure the container cover to its base. Upon entry of corresponding retrieve data into the CPU and the CPU determining that there is a "match" between the insert data and retrieve data the electric lock is operated by the CPU to permit access to the secure space within the container and retrieval of the article or articles therein. Such article or articles may be units of blood or uman organs to be "matched" to the patient to receive same or crime scene evidence for which a "chain of custody" is required or similar articles.

12 Claims, 3 Drawing Sheets

"MATCH" CONTROLLED CONTAINER

CROSS REFERENCE TO RELATED APPLICATIONS

This application claims the benefit of prior filed and Provisional Patent Application 60/581,108, filed Jun. 18, 2004 for Match Controlling Security And Safety System.

BACKGROUND OF THE INVENTION

1. Field of Application

This invention relates to the safety and security of articles; and more particularly to "match" controlled securement, and release from securement, of such articles.

2. Description of Prior Art

There are things, articles, which are found, located, stored, etc. at one location and that are to be moved to another location for specific purposes, and which must be secured while being so moved and then made available only for the specific purpose and probably by a person with authority to access the article for the specific purpose. One such thing, article, etc. may, for example, be one or more bags of blood found to "match" at a hospital, or from a blood supplier for a hospital, for infusing a "matched" patient or for possible use by a physician for a "matched" patient undergoing an operation. Another such thing or article might be "matched" human organs taken from a donor at one hospital and destined for a surgeon's use for a "matched" recipient at another hospital. While yet other such things or articles could be items of evidence from a crime scene that are to be transported in a secure manner to a police station, lab or prosecutor's office.

The use of blood and blood products, for example, continues to be the mainstay of therapy for surgical bleeding and trauma. Currently, when blood is required in the operating room or other hospital areas, a nurse or orderly is dispatched to the blood bank to retrieve type-specific blood for the patient. In general, a form of patient identification is presented by the nurse or orderly to the blood bank technician who, in turn, retrieves the required type-specific blood from the blood bank based on the patient's blood-type. The blood or blood products are then distributed a single unit at a time or as multiple units (in a cooler) to the nurse or orderly. The distributed blood products are then carried back to the site of therapy by the nurse or orderly where the personnel who will be administering the blood or blood products must check them for compatibility with the intended patient. The conventional process of checking blood requires one person to read aloud the intended patient's name, his hospital ID number, their blood product unit number, the blood product type, and the expiration date of the blood—while another person verifies this information as being correct for that particular intended recipient. However, despite these safety checks, it is still possible to administer the wrong blood to a patient and transfusion reactions due to blood-type incompatibility still occur [as demonstrated, for example, by Mybre B A and McRuer D., "Human error-a significant cause of transfusion mortality", *Transfusion* 40:879-885 (2000); Blumberg N. and Heal J. M., "ABO mismatched platelet transfusions and concise outcomes after cardiac surgery", *Transfusion* 42:166-172 (2002)]. Additionally, in busy medical centers with multiple containment coolers being dispatched to the operating room for administration to different patients, the potential continues to exist for the wrong container of blood to arrive in an operating room and be given mistakenly to an incompatible patient.

Also, with the ever-increasing frequency and growth of organ transplantation, a similar safety problem exists in making sure that correctly matched and type-compatible donor organs arrive at the intended recipient's location without error. Indeed, a highly publicized instance of a patient at Duke University who received incorrectly matched organs and subsequently died as a result, underscores the continuing need for an entirely new safety technology which is more reliable. Currently however, organs for transplantation are transported in unlocked containment coolers with the type-specific identification information merely taped to the outside of the carrier container. Moreover, no security device or safety means are in place within such containers to prevent tampering; and no access control device or security measures currently exist to prevent inadvertent mismatching and incompatibility between the type-specific organs then held within the containment cooler and the type-specific requirements of the person intended to receive the donated organ.

Currently, articles such as crime scene evidence, intended for court trial is often tracked using paper records (each person in possession signs his/her name); and no security devices are presently used to prevent tampering (or even destruction) during the custody and/or transport of of such physical evidence articles. There are, however, requirements in the legal field for identifying sequentially and recording chronologically those people who have been in possession of physical evidence (tissue, bullet fragments, bodily fluids, etc.), which will (or might) be used for a court trial. This is typically called the requirement for "chain of custody" evidence and allows the court to track all people who handle (or mishandle) the physical evidence. Yet, no device exists to date which provides both security and "chain of custody" record information for such evidence.

There are known containers specifically for use in transporting medical articles, but such containers, as shown and described in U.S. Pat. No. 4,951,482 of Aug. 28, 1990 granted to G. L. Gilbert for "Hypothermic Organ Transport Apparatus" and U.S. Pat. No. 5,157,930 of Oct. 27, 1992 granted to S. C. McGhee and others for "Organ Preservation Apparatus" do not provide for any locking arrangement whatsoever and thus thus do not restrict access to the containerized article unless there is a "match" correlating the recipient with a donor or the article. There are also known containers that lock but such containers, as shown and described in U.S. Pat. No. 6,133,842 of Oct. 17, 2000 granted to J. Garlepy for "Alarm System For Portable Container" only provide an alarm should the container move, tilt or its cover be opened while U.S. Pat. No. 6,430,689 of Aug. 6, 2002 granted to J. M. Lacombe for "System For Securely Transporting Objects in A Tamper-Proof Container, Wherein At Least One Recipient Station Is Mobile and Portable" requires input from a remote host in order to access the container contents. Neither of these types of containers are suitable.

There are mechanical locks that are intended for use with units of blood to restrict access to the blood to a particular recipient such as shown and described in U.S. Pat. No. 4,787,222 of Nov. 29, 1988 granted to C. A. Irazoqui and others for "Combination Lock For Blood Identification System" and U.S. Pat. No. 4,265,101 of May 5, 1981 granted to H. Kaplan for "Blood Identification Means"; and even a computer controlled lock as shown and described in U.S. Pat. No. 4,415,802 of Nov. 15, 1983 granted to G. R. Long for "Cross Identification System And Lock". These locks and locking systems are, however, particularly adapted for articles such as units of blood and do not require all the inputs for an acceptable "match" before access to the article becomes available.

Computer controlled medical carts are also known. However, carts of the type shown and described in U.S. Pat. No. 4,967,928 of Nov. 6, 1990 granted to C. L. Carter for "Inventory Control Including Individual Patient Listing and Medical Chart Record For Medication Cart" and in U.S. Pat. No. 6,339,732 of Jan. 15, 2002 granted to F. H. Foon and others for "Apparatus And Method For Storing, tracking And Documenting Usage Of Anesthesiology Items" are primarily intended for record keeping and billing purposes. In addition the storage of many articles for many intended recipients could very well result in release and use of an article for an unintended recipient, with possible life threatening repercussions.

Also known are highly computerized systems such as shown and described in U.S. Pat. No. 4,835,372 of May 30, 1989 granted to P. P. Gombrich and others for "Patient Care System" that require relatively complex equipment that must be accessible throughout a hospital and that merely correlates a recipient and their medications but does not restrict access to the medication article unless there is a "match"; as well as that shown and described in U.S. Pat. No. 5,272,318 of Dec. 21, 1993 granted to J. G. Gorman for Electronically Readable Medical Locking System" that broadly refers to a lock without describing or even suggesting: the environment where such lock would be disposed; how such lock would be employed; what such lock would interact with and how such interaction would occur to effect the locking and unlocking action. More importantly this system would be unacceptable because the end result of a "match" would be to merely display the code required to unlock the lock and that for only a short period of time.

BRIEF SUMMARY OF THE INVENTION

It is therefore an object of this invention to provide a new and novel article container.

It is another object of this invention to provide a new and novel article container which is responsive to "match" control to permit access to article(s) within the container.

It is yet another object of this invention to provide new and novel containers that are suitable to securely receive an article or articles, which may constitute a unit or units of blood, and which only permit access to the secured articles in the container upon a "match" between the article(s) secured within the container and the permitted recipient for the article(s).

It is still another object of this invention to provide new and novel containers that are suitable to securely receive an article or articles, which may constitute a body organ or organs, and which only permit access to the secured articles in the container upon a "match" between the article(s) secured within the container and the permitted recipient for the article(s).

It is yet still another object of this invention to provide new and novel containers that are suitable to securely receive an article or articles, which may constitute a human organ or organs, and which only permit access to the secured articles in the container upon a "match" between the article(s) secured within the container and the permitted recipient for the article(s).

It is a further object of this invention to provide new and novel containers that are suitable to securely receive an article or articles, which may constitute evidence for an investigation by city, state and/or federal authorities, and which only permit access to the secured articles in the container by authorized personnel and provide a "chain of custody" for the respective article(s).

The present invention provides an individual access controlling security system as well as a content safety system; and is an apparatus and assembled device useful with any sealable on-demand container having determinable dimensions and configuration, an enclosed spatial volume, and a closure mechanism which can be opened and closed at will. The sealable container is typically a configured housing having means for keeping its internal contents cool or cold, or warm or hot; and is commonly fitted with a hinged lid. The security and safety system of the sealable container comprises an electronic lock system equipped with an onboard programmable computer capable of operating and opening the electronic lock system only when specific person identity parameters and technical data and type-matching requirements are met and matched completely, these particulars being system reference standards which are pre-chosen and fixed in advance Other objects, features and advantages of the invention in its details of construction and arrangement of elements and systems will be seen from the above and from the following description of the preferred embodiments when considered in conjunction with the accompanying drawings and appended claims.

DETAILED DESCRIPTION OF THE PREFERRED EMBODIMENTS

Figure 1:
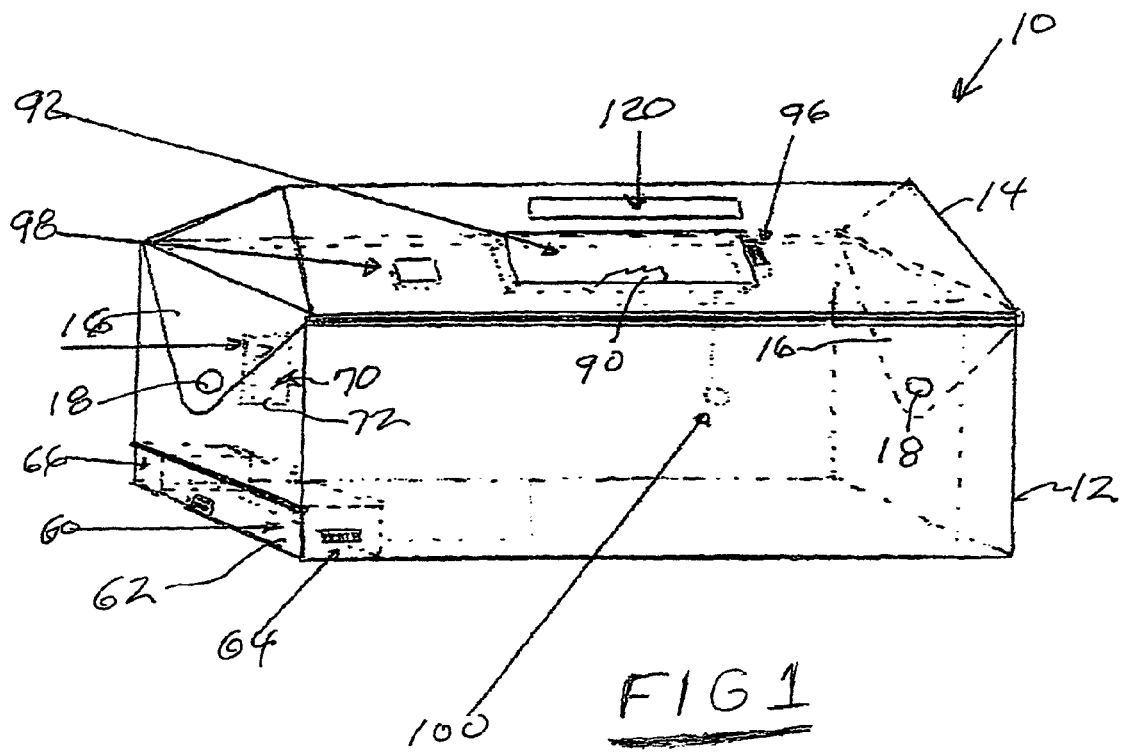
FIG. 1 is a perspective sketch of a container incorporating the instant invention with its top cover in place atop the container.
Figure 4:
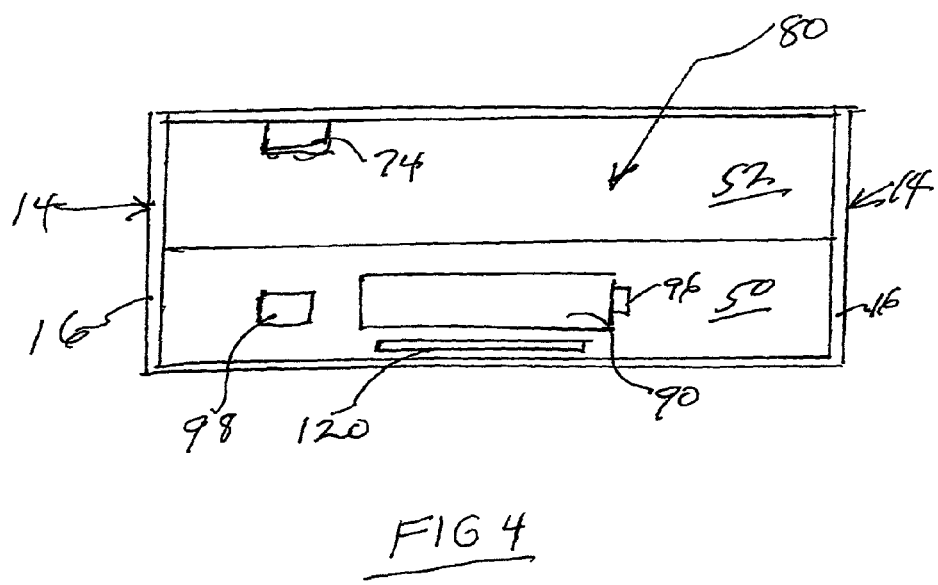
FIG. 4 is a bottom view of the top cover of the container of FIGS. 1-3 removed from the base section of the container.

One preferred embodiment of the instant invention comprises a sealable container with a hinged lid and a closure mechanism which provides an enclosed insulated space of fixed size and predetermined volume; and an electronic control apparatus equipped with an onboard computer capable of operating an electronic lock system. The security and safety system will typically include: a palm PC sized rechargeable, battery powered central processing unit (CPU) which is optionally integrated into the wall or top of the container; a viewable display screen optionally integrated into the top or a wall of the container; an optional temperature probe mounted on the interior surface of the container and interfaced to the CPU; a rechargeable battery-powered locking system also interfaced with the CPU; an infrared and hard wired data port also interfaced to CPU; audible alarm hardware; a transmitter; reference standard software and access request software able to be programmed with user names/IDs, patient name/ID, product name/ID, expiration dates, ABO/HLA blood-type; at least one comparative software program to compare and to match the inputted information and data against the pre-chosen reference standards; and a general comment field.

The security and safety system preferably also incorporates and utilizes time/date software programs. Such time/date software will allow information to be entered at will into the CPU; and will operate the locking mechanism (to open) only when precisely set critical fields "match" exactly and completely with reference standards chosen in advance. Also, an alarm algorithm will be activated under any of these circumstances or events: if the battery life declines below 20%; if the container has been away from the primary source or location (a blood bank, a crime scene, an organ bank, etc.) for a user-defined and pre-chosen period of time; and if the container lid is open or the container remains unlocked for greater than a user-specified and pre-chosen maximum time period.

The internal computer of the security and safety system can be programmed at will in the blood bank or organ bank by a laboratory technician with the intended reference standard information and data including the intended patient's name and personal identification numbers. The system may also be programmed with the authorized user's name and ID number. Such programming can be done conventionally using a bar code pen (optional) or a direct hospital/lab computer to on-board CPU via an infrared or hard wired port. Once programmed and locked, the articles within the container can only be accessed by an authorized user entering their requisite ID number/name; and then entering the required and precisely identified intended patient and product name information and data. Once proper authorized user and intended patient information input has occurred, a viewing screen or monitor identifying the internal contents of the container becomes activated. The authorized user then enters specific technical information and data into the on-board computer from paperwork previously supplied by the blood bank/organ bank. Such technical information and data also must "match" exactly and completely with the referenced standard information and data internally held within the computer. If and only when all the inputted technical data "matches" and corresponds exactly with the internal reference standard programmed data will the security and safety system of the container then operate and unlock the closure mechanism to allow access to the container's contents. Additionally, the internal computer is capable of tracking each authorized user (s) by user-specific identification numbers/names and time of access or interaction. These system features are illustrated, by way of example, in the following FIGS. 1 thru 4.

Figure 2:
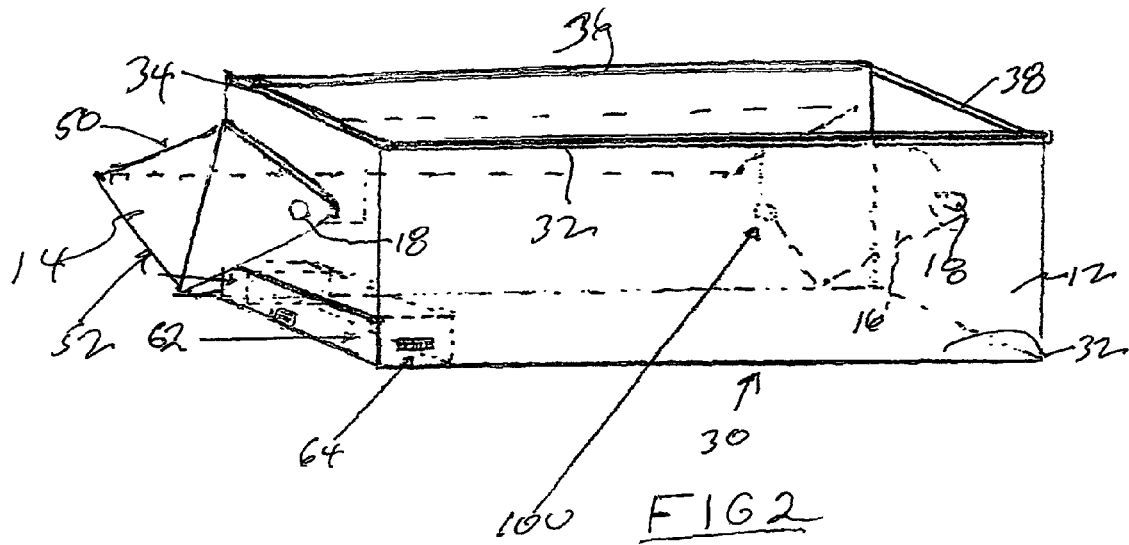
FIG. 2 is a perspective sketch of the container of FIG. 1 with its top cover open.
Figure 3:
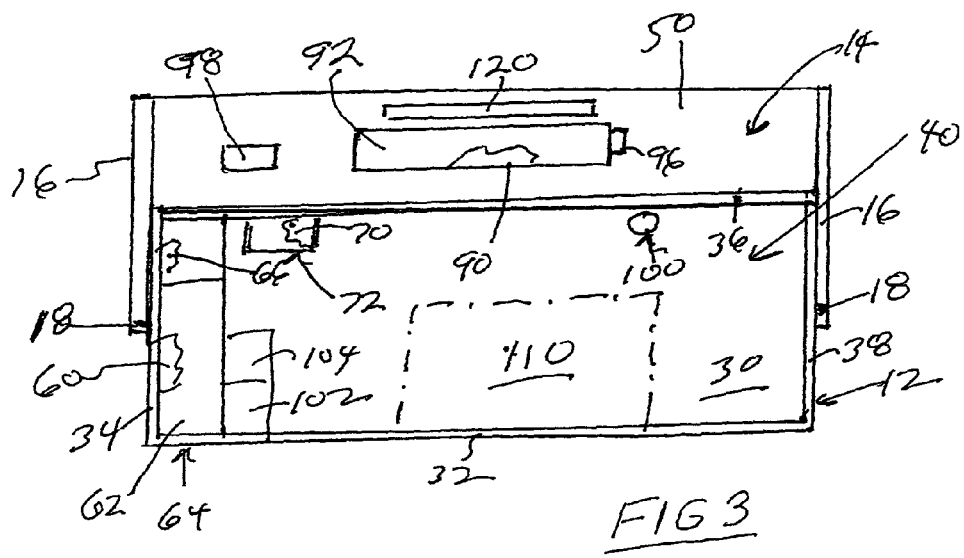
FIG. 3 is a top view of the open container of FIG. 2.

With reference to FIGS. 1-3 there is generally shown at 10 a secure container with a base section 12 and a top cover 14 hingedly mounted to base section 12 by arms 16 and pivots 18. Base section 12 includes a bottom panel 30 (FIGS. 2 and 4) and side walls 32, 34, 36 and 38 connected together and rising up from bottom panel 30; which are suitably fabricated from appropriate to preferably provide an insulated space 40 above bottom panel 30 and within side walls 32, 34, 36 and 38. Top cover 14; is fabricated from materials similar to those of base section 12; is sized to fit over and coact with base section 12 to provide a closure for same and to form with base section 12 a closed security container 10; and is configured as a peaked gable to facilitate viewing of and access to components of the secure container as will be further explained. While top cover 14 has been shown in a peaked gable configuration with top panels 50, 52 (FIGS. ! and 4) it should be understood that it could just as well be fabricated with a single flat top panel, or with a single flat top panel and depending sides, or in any other suitable and appropriate configuration to function as a closure for base section 12. The respective sizes of bottom panel 30 and side walls 32, 34, 36 and 38 and of top panels 50,52 of top cover 14 are selected depending upon the various components associated with container 10 and their size and placement with respect to base section 12 and top cover 14 as well as the size and volume of the articles to be placed within container 10.

A conventional rechargeable battery 60 (FIGS. 1 and 3), of suitable voltage and other characteristics, is housed in a battery compartment 62 within base section 12. A Battery recharge outlet 64 is provided for battery 60 to connect battery 60 to a suitable source of recharge power in a conventional way. A tracking transponder 66 is also provided within base section 12. A first portion 70 (FIGS. 1 and 3) of an electronically operated lock 72 is positioned within base section 12 for co-action with a second portion 74 of lock 72. positioned within a space 80 (FIG. 4) of top cover 14. Suitable conductive wiring (not shown) interconnects battery 60, with transponder 66 and electronically operated lock 72 lock to provide them with operating power.

A CPU 90 (FIGS. 1, 3 and 4) is housed within space 80 of top cover 14 and is electrically connected to battery 60 for its operating power. CPU 90 includes a touch screen 92. (FIGS. 1 and 3) to facilitate data entries into CPU 90. A data port 96 and an infra-red data port 98 are also housed within space 80 of top cover 14 and are suitably and appropriately connected to CPU 90 for interaction therewith to input data into CPU 90. Touch screen 92, data port 96 and infra red data port 98 are placed for access in top panel 50 of top cover 14 as shown in FIG. 1 to facilitate relatively easy access by the user to touch screen 92, and data ports 96 and 98. Also included within base section 12 of container 10 is a thermister 100 conventionally powered and co-acting with CPU 90 to provide temperature data thereto. Suitable and conventional cooling 102 (FIG. 3) and heating devices 104 may also be housed within container 10 to facilitate providing a suitable environment within space 40 for an article 110 (shown in phantom in FIG. 3) which could be one or more units of blood, an organ or organs or other Item requiring a temperature and/or humidity controlled environment. A handle 120 (FIGS. 1, 3 and 4) of suitable material, fabrication and configuration is also provided for container 10 and is preferably located in top panel 50 of top cover 14.

Figure 5:
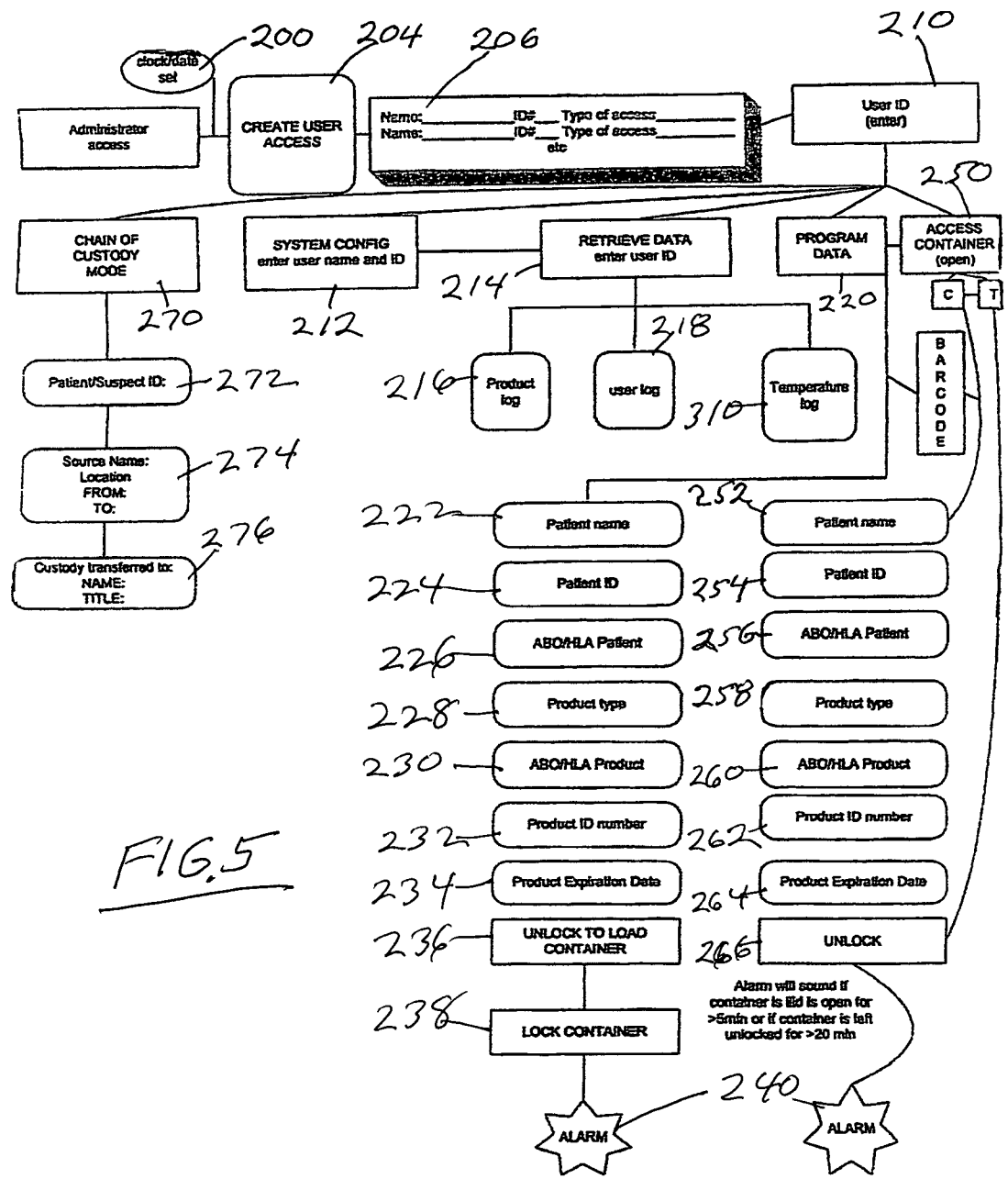
FIG. 5 is a block diagram of a preferred embodiment of the instant invention.

Some examples of use for Container 10 will be explained with reference to FIG. 5. The person in charge, administer, accesses CPU 90 at 200 enters and sets the clock/date at 202 and creates user access at 204 with one or more user names, IDs and the type of access to be permitted for respective users at 206. A permitted user at 210 enters their ID which is transmitted to System Config at 212 and to Retrieve data at 214 which includes the Product Log at 216, User Log at 218 and Temperature Log at 220.

When a user, such as a lab technician where unit(s) of blood might be the intended article(s). or a nurse or surgeon where human organs are to be shipped in a secure container 10, is to put an article into a secure container 10 they enter their ID at 210 and proceed through Program Data at 220 to enter: the Patients Name at 222; the patients ID at 224; ABO/HLA for the patient at 226; the Product type at 228; the ABO/HLA for the Product at 230; the Product ID Number at 232; the Product expiration Date at 234 and Container 10 is unlocked at 236 to permit loading of the article into Container 10. Thereafter Container 10 is locked at 238 and prepared for transportation to the intended users physician or nurse. The Alarm at 240 will sound if top cover 14 of container 10 is left open for more then 5 minutes or if container 10 is left unlocked for more then 20 minutes.

When container 10 with an article locked inside is received at the place of intended use the physician or nurse whose ID has been entered into the system enters their ID at 210 and proceed through Access Container (open) at 250 to enter: the Patients Name at 252; the Patients ID at 254; ABO/HLA for the Patient at 256; the Product Type at 258; the ABO/HLA for the Product at 260; the Product ID Number at 262; the Product expiration Date at 254 and Container 10 is unlocked at 256 to provide access to the article in Container 10.

Thus, only when all the user-inputted information "matches" precisely in every respect with the programmed reference standard information and data of the security system will electronic lock 70 of container 10 be unlocked and the person be given access to the internal article secured within container 10.

It should be recognized and appreciated, therefore, that the present invention offers many major features not previously available. After the security and safety system has been programmed with the pre-chosen reference standard information and data and the contents of the container locked in place, the closure mechanism of the sealed container can only be opened by an authorized user or recipient who has been pre-chosen in advance. Additionally if desired, CPU 90 and software programs of the on-board security and safety system are capable of recording and tracking each authorized recipient/user over time who has obtained access to the internal contents of the sealed container 10 by retaining each set of user specific identification information and data as well as the date and time of access and the length of interaction.

Moreover, if and when used in "chain of custody" mode, as at 270, 272, 274 and 276, such as for legal purposes and physical evidence at court trial, the programmed security-safety container 10 can be opened by a scene of the crime police officer/agent in the field who has found or gathered articles of physical evidence. Security-safety container 10 is opened by entering and inputing specific information into CPU 90; the articles of physical evidence are placed inside container 10; and container 10 is then sealed and locked in accordance with programmed reference standard identity information, technical data of the contents and personal access control particulars. Subsequently, only specifically authorized persons who can enter and precisely "match" all the requisite personal information and access data requirements of the reference standards program will be able to reopen security-safety container 10. Also if desired, on-board CPU computer 90 can be programmed and set to track and record each person who was able to access the internal article contents of container 90, as well as the length of time each person was in legal possession and custody of container 90 and its contents.

In another embodiment of the invention disposable plastic bags for blood products, organs, and evidence are manufactured with a computer chip comprising the electronic control apparatus. The chip records and stores product data (such as temperature) and sends this data to the onboard computer if the product is returned to the container without being used. The chip also sends signals to the computer when the bag is removed from the container, which is then time coded. If the unit is removed but not used and then replaced in the container, the chip sends signal (and stored data) to the computer when the bag is replaced. This allows the blood bank to determine the length of time the unit has been out of the container and the temperature of the product during its absence.

In yet another embodiment of the invention disposable plastic bags are manufactured with a plastic-ring which is placed over a spindle in the container. When the bag is removed from the spindle, a signal is sent to the onboard CPU. The ring is located in such a position that it must be used/destroyed in order to use the product (such as making the ring an integral part of the injection port covering (which must be removed) on a bag of blood). For blood products only. The container has individual CPU controlled electronically locking compartments inside into which each bag of blood is inserted. The lid on each compartment is capable of sending a time stamped signal to the computer when opened. If the blood is used, the bag is thrown away as usual. If the blood is returned to the compartment, the compartment lid sends another time stamped signal to the computer. A bar code pen or other infrared data transfer device could also be interfaced with the onboard CPU to allow transfer of patient and product information between mainframe computers (such as in the blood/organ bank) and the onboard CPU.

In an alternative embodiment of the "Chain of custody" mode: the container can be opened by police officer/agent in the field gathering evidence. The evidence is placed inside the container. The officer/agent enters relevant crime seen information and locks the container. Only authorized personnel can reopen the container. In addition, the computer can be set to record each person who handles the container and the time each person was in possession of the container. A SMART-BAG could be manufactured for the chain of custody mode: a permanently sealed evidence bag with chip would send a signal to the computer if the bag were removed, thus allowing recognition of possible tampering during transport.

From the above description it appears that there is no similar portable computerized technology currently known or available for the purposes described herein. The invention offers significant improvement and advantages in both patient safety and blood/tissue banking quality assurance in the following ways:

1. patient safety will be improved because once programmed with user names and ID numbers and the patient's name and hospital ID number in the blood bank or tissue bank the only way to access the products in the cooler will be to provide the computer with the user ID and name, the intended patient's name and ID number, and the product name and ID number at the point of delivery. In addition, if the software function, which allows tracking and timing of users, is enabled, a report can be generated of all users accessing the storage container and time of access;

2. the device will be capable of monitoring temperature inside the storage container. Temperature data can be downloaded by blood bank or organ bank personnel, which would allow a record to be kept of product storage temperature over time. This would be useful for blood/tissue bank quality assurance allowing a record of storage temperature to be maintained even after products have left the blood bank or organ bank and up until the time of administration; and 3. the device will provide for secure storage and transport of forensic and other evidence for legal cases and is capable of providing a "chain of custody" by tracking and recording each user's by name and/or ID number.

It is understood that although there has been shown and described preferred embodiments of the invention that various modifications may be made in the details thereof without departing from the spirit as comprehended by the following claims.

What is claimed is:

1. A "match" controlled, hand carryable and portable, security container for transport of medically related articles, comprising:
   a) hand portable container means providing a securable space of predetermined volume and configuration to receive one or more medical related articles;
   b) said container means being of a size, configuration and weight to facilitate being hand carried and having base means and cover means that together form between them a securable space;
   c) computer operated lock means assembled to, and as a part of, said container means to control access to said securable space by either locking said base means and cover means together to restrict access to said securable space, or by releasing said cover means and said base means from each other, to permit access to said securable space;

d) computer means carried by said container means for operating said lock means;

(e) battery power means carried by said container means for providing operating electric power to said computer means and said lock means;

(f) data entry means carried by said container means for the entry of data into said computer means, i) whereby insert data, relative to the articles that are to be placed into said securable space, when entered into said computer means, facilitates locking of said cover means to said base means; and ii) whereby retrieval data, relative to the article or articles that are placed into said securable space, when entered into said computer means facilitates release of said cover means from said base means;

g) said computer means being configured to determine a "match" between insert data and retrieval data, and only upon determining that there is a "match" between said insert data and said retrieval data, to effect operation of said lock means to permit opening of said hand portable container means and access to an article or articles therein; and h) wherein the article or articles to be placed within said securable space are units of blood and the "match" is between the blood of the units of blood and the blood of a person for whom the units of blood are to be used.

2. The hand carryable and portable security container of claim 1; wherein data port means and infrared data port means are carried by said container means and are respectively connected to said computer means to facilitate entry of data into said computer means.

3. The hand carryable and portable security container of claim 1; wherein said electric power means comprises rechargeable battery means for providing electric power and outlet means for connecting said rechargeable battery means to a source of electric power to be recharged thereby.

4. The hand carryable and portable security container of claim 1; wherein said data entry means and said computer means are carried by said cover means and said cover means is configured as a gable to facilitate viewing and access of said data entry means.

5. The hand carryable and portable security container of claim 1; wherein the article or articles to be placed within said securable space are items found at a crime scene and wherein said computer means is configured to provide a "chain of custody" for said crime scene items.

6. The hand carryable and portable security container of claim 1; wherein said computer means is configured to receive a user ID and will not provide said "match" unless the user ID is included in both said insert data and said retrieval data.

7. A "match" controlled, hand carryable and portable, security container for transport of medically related articles, comprising:

a) hand portable container means providing a securable space of predetermined volume and configuration to receive one or more medical related articles;

b) said container means being of a size, configuration and weight to facilitate being hand carried and having base means and cover means that together form between them a securable space;

c) computer operated lock means assembled to, and as a part of, said container means to control access to said securable space by either locking said base means and cover means together to restrict access to said securable space, or by releasing said cover means and said base means from each other, to permit access to said securable space;

d) computer means carried by said container means for operating said lock means;

(e) battery power means carried by said container means for providing operating electric power to said computer means and said lock means;

(f) data entry means carried by said container means for the entry of data into said computer means, i) whereby insert data, relative to the articles that are to be placed into said securable space, when entered into said computer means, facilitates locking of said cover means to said base means; and ii) whereby retrieval data, relative to the article or articles that are placed into said securable space, when entered into said computer means facilitates release of said cover means from said base means;

g) said computer means being configured to determine a "match" between insert data and retrieval data, and only upon determining that there is a "match" between said insert data and said retrieval data, to effect operation of said lock means to permit opening of said hand portable container means and access to an article or articles therein; and h) wherein the article or articles to be placed within said securable space are human organs and the "match" is between the human organs and the person that is to receive those human organs.

8. The hand carryable and portable security container of claim 7; wherein a data port and an infrared data port are carried by said container and are respectively connected to said computer to facilitate entry of data into said computer.

9. The hand carryable and portable security container of claim 7; wherein said source of battery electric power comprises at least a rechargeable battery and an outlet for connecting said rechargeable battery to a remote source of electric power to be recharged thereby.

10. The hand carryable and portable security container of claim 7; wherein said data entry device and said computer are carried by said cover and said cover is configured as a gable to facilitate viewing and access of said data entry device.

11. The hand carryable and portable security container of claim 7; wherein the article or articles to be placed within said securable space are items found at a crime scene and wherein said computer is configured to provide a "chain of custody" for the crime scene items.

12. The hand carryable and portable security container of claim 7; wherein said computer means is configured to receive a user ID and will not provide said "match" unless the user ID is included in both said insert data and said retrieval data.

* * * * *